(12) United States Patent
Bornstein

(10) Patent No.: US 7,621,745 B2
(45) Date of Patent: Nov. 24, 2009

(54) USE OF SECONDARY OPTICAL EMISSION AS A NOVEL BIOFILM TARGETING TECHNOLOGY

(75) Inventor: Eric Bornstein, Natick, MA (US)

(73) Assignee: Nomir Medical Technologies Inc., Waltham, MA (US)

( * ) Notice: Subject to any disclaimer, the term of this patent is extended or adjusted under 35 U.S.C. 154(b) by 741 days.

(21) Appl. No.: 10/961,796

(22) Filed: Oct. 8, 2004

(65) Prior Publication Data

US 2008/0058908 A1    Mar. 6, 2008

Related U.S. Application Data

(60) Provisional application No. 60/509,685, filed on Oct. 8, 2003.

(51) Int. Cl.
*A61C 5/00* (2006.01)
*A61C 15/00* (2006.01)
*A61C 5/02* (2006.01)
*A61C 1/00* (2006.01)

(52) U.S. Cl. ................ 433/215; 433/29; 433/224

(58) Field of Classification Search ......... 433/214–224, 433/29

See application file for complete search history.

(56) References Cited

U.S. PATENT DOCUMENTS

| | | | | |
|---|---|---|---|---|
| 5,098,427 A | * | 3/1992 | Hessel et al. | 606/11 |
| 5,271,734 A | * | 12/1993 | Takeuchi | 433/72 |
| 5,324,200 A | * | 6/1994 | Vassiliadis et al. | 433/224 |
| 5,611,793 A | * | 3/1997 | Wilson et al. | 606/2 |
| 5,616,141 A | * | 4/1997 | Cipolla | 606/15 |
| 6,179,830 B1 | * | 1/2001 | Kokubu | 606/16 |
| 6,387,977 B1 | * | 5/2002 | Sawhney et al. | 522/184 |
| 6,395,016 B1 | | 5/2002 | Oron et al. | |
| 6,558,653 B2 | * | 5/2003 | Andersen et al. | 424/49 |
| 2002/0186921 A1 | * | 12/2002 | Schumacher et al. | 385/31 |
| 2003/0059738 A1 | | 3/2003 | Neuberger | |
| 2004/0034341 A1 | * | 2/2004 | Altshuler et al. | 606/3 |
| 2004/0114860 A1 | * | 6/2004 | Dultz et al. | 385/31 |
| 2004/0210276 A1 | * | 10/2004 | Altshuler et al. | 607/88 |
| 2004/0224288 A1 | | 11/2004 | Bornstein | |

FOREIGN PATENT DOCUMENTS

| WO | WO 00/62701 A | 10/2000 |
|---|---|---|
| WO | WO 00/74587 A | 12/2000 |

OTHER PUBLICATIONS

International Search Report for related PCT Application No. PCT/US2004/33431, dated May 1, 2006, 3 pages.
Written Opinion of the International Searching Authority for related PCT Application No. PCT/US2004/33431, dated May 1, 2006, 5 pages.
PCT International Search Report—(PCT/US07/16613) Date of Mailing Sep. 12, 2008.
Supplementary Partial European Search Report—(EP 04 79 4705) Date of Mailing May 15, 2009.

* cited by examiner

*Primary Examiner*—Ralph A Lewis
*Assistant Examiner*—Yogesh Patel
(74) *Attorney, Agent, or Firm*—John M. Garvey; Matthew L. Fenselau; Foley & Lardner LLP

(57) ABSTRACT

Provided herein are methods and compositions useful for the treatment of periodontal disease exploiting optical and thermal emissions of near-infrared laser systems and fibers in order to target chromophore-stained biofilm while minimizing damage to healthy tissues.

14 Claims, 6 Drawing Sheets

USE OF SECONDARY OPTICAL EMISSION AS A NOVEL BIOFILM TARGETING TECHNOLOGY

CROSS REFERENCE RELATED APPLICATIONS

This application claims priority to U.S. Ser. No. 60/509,685 filed on October 8, 2003.

BACKGROUND

1. Field of the Invention

The present invention relates to live biofilm targeting and subsequent bacterial thermolysis for its eradication in the human body, utilizing secondary quantum optical and thermal emissions from the distal end of near infrared laser delivery fibers.

2. Relevant Technologies

To date, in excess of 300 different species of bacteria have been described in the human oral cavity (Moore W. E., *The Bacteria of Periodontal Diseases*, Periodontol. 2000). Most bacteria are found in dental plaque and in the sub-gingival periodontal and periimplant pockets. These sub-gingival bacteria have evolved to fight and inhibit the normal host defense system creating a unique ecological niche in the periodontal pocket.

Subgingival bacteria find their nutrient base in the crevicular fluid of the periodontal pocket. Even though these bacteria are in direct proximity to the highly vascularized periodontal and periimplant epithelium, they continue to grow and thrive. Despite (and arguably because of) the host's immune and inflammatory responses seeking to inhibit bacterial colonization and intrusion into the tissues (e.g., mediated by lysozymes, complement formation, bradykinin, thrombin, fibrinogen, antibodies and lymphocytes), subgingival bacteria tend to prevail in the periodontal and/or periimplant pocket providing a unique environmental niche (Cimasoni, Monogr. Oral Sci. 12:III-VII, 1-152 (1983)).

To successfully treat the periodontal and/or periimplant pocket and periodontal/periimplant disease as a whole, the local inflammation and its cause must be eliminated, in an effort to re-establish an intact barrier against the root of the tooth. A newly regenerated periodontal ligament or epithelial barrier connected to the root of the tooth or implant will limit the space available for bacterial growth. Once the cause of the immune and inflammatory responses is eliminated, the periodontal tissues will likely heal. When dealing with implants, the disease is even more recalcitrant and difficult to eliminate, because of the unique and foreign three dimensional architecture and roughened surface of most commercial dental implants.

Healing can be seen as new collagenous and epithelial attachments begin to form in the area just inferior to the base of the periodontal pocket. These new periodontal ligament fibers generally occur only in areas not previously exposed to live bacteria in the pocket. In contrast, the epithelial seal known as long junctional epithelium (i.e., a strong epithelial adaptation to the root surface) generally will occur in areas that were exposed to the live biofilm of the periodontal pocket. With implants (where a periodontal ligament does not exist) new bone formation and/or long junctional epithelium are sought to reduce the available space for bacterial growth.

Traditional Approaches

Periodontal/periimplant instruments have been invented and designed over the years for the specific goal of plaque and calculus removal, root planing and debridement, and removal of diseased periodontal/periimplant tissues. In particular, periodontal scaling, root planing and curettage instruments are the mechanical approaches of choice to remove dental plaque, calculus, diseased cementum, and diseased pocket soft tissues.

A number of pharmacological approaches have been developed as an adjunct to traditional mechanical approaches to attack bacteria (e.g., extended release antimicrobial formulations for delivery in the periodontal/periimplant pocket after mechanical debridement). However, these pharmacological modalities have significant limitations because to be effective they must (a) reach the intended site of action (a deep three-dimensional pocket), (b) remain at an adequate concentration, and (c) last for a sufficient duration of time.

To remain at an adequate concentration and last for a sufficient duration of time, the intrasulcular delivery vectors of the antimicrobials (e.g., resorbable gels, resorbable microspheres, and antimicrobial impregnated chips) must fill the physical space of the periodontal pocket. Most of these vectors stay in place in the periodontal pocket for the duration of the drug delivery therapy (up to three weeks), and hence prevent the immediate healing process of new periodontal attachment and long junctional epithelium formation at the tooth/implant pocket interface after mechanical debridement. In addition, the majority of local antimicrobials used are bacteriostatic, and never fully eliminate periodontal and/or periimplant pathogens from the treatment site. Long term resistant strains often arise in the periodontal pocket in response to sub-lethal antimicrobial absorption. Not surprisingly, these local pharmacological modalities have been reported to have only marginal success rates (*The Role of Controlled Drug Delivery for Periodontitis*, Position Paper from AAP, 2000) and to have severe limitations ultimately leading to re-infection and continued disease progression.

Recent Developments: The Biofilm Paradigm

The recognition that subgingival dental plaque exists as a living biofilm has shed some light on the underlying mechanism at work (*Periodontology* 2000 (supra); and Chen, J. Calif. Dent. Assoc. (2001).

Costerton et al., J. of Bacteriol. (1994), have described biofilms as matrix enclosed bacterial populations adherent to each other and/or to surfaces or interfaces. The same researchers have also described biofilms as ecological communities that have evolved to permit survival of bacterial the community as a whole, with specialized nutrient channels within in the biofilm matrix (a primitive circulatory system) to facilitate the movement of metabolic wastes within the colony. If dental plaque and subgingival bacterial colonies are now viewed as a living biofilm, there is a need (not only limited to dentistry) for effective biofilm targeting techniques.

Current understanding of biofilms has conferred upon them some basic properties (Marsh et al., Adv. Dent. Res. (1997)). These include but are not limited to actual community cooperation between different types of microorganisms, distinct and separate microcolonies within the biofilm matrix, a protective matrix surrounding the bacterial colonies, different distinct microenvironments within different microcolonies, primitive communication systems, and unique protection from and resistance to antibiotics, antimicrobials, and the immunological and inflammatory host response.

Most previous attempts to control periodontal diseases have been performed based on traditional understanding of periodontal and periimplant bacteria in in vitro. As a living biofilm (in vivo) however, subgingival plaque and periodontal bacteria act and function quite differently than the classical laboratory models would predict. Periodontal and periimplant bacteria in a live biofilm produce different and more harmful chemicals and enzymes than they do in culture in the laboratory. Also, within a biofilm, there is an increase in the spread of antibiotic resistance through inter-species relationships.

The biofilm (a proteinaceous slimy matrix) itself serves as an effective barrier of protection from many classical therapeutic regimens targeting bacteria. Antibiotics may fail to even penetrate the biofilm and reach the causative bacteria if they are neutralized by resistant enzymatic reactions within the biofilm.

This new understanding of the ethiology underlying periodontal disease has thus identified a void and a need for novel procedures targeting the biofilm directly to combat periodontal disease and the recalcitrant biofilms that harbor and protect the pathogenic bacteria. Such techniques are hereinafter referred to as Biofilm Targeting Technologies (BTT).

Various dyes and other compounds have been proposed for the express purpose of disinfecting or sterilizing tissues in the oral cavity. It has been proposed to selectively target bacteria for laser irradiation with chromophores in the oral environment to expedite bacterial thermolysis. Specifically, there are proposals for treating inflammatory periodontal and periimplant diseases along with other lesions in the oral cavity, by: (a) contacting the tissues, wound or lesion, with a redox agent (dye) such that the bacteria themselves take up the compound, and are inhibited over time, by the exogenous agent in the absence of a laser; or by (b) contacting the tissues, wound or lesion, with a photosensitizing compound (dye) such that the bacteria and/or tissues themselves take up the compound, and then irradiating the tissues or lesion with laser light (generally soft visible red lasers) at the specific wavelength absorbed by the photosensitizing and targeting chromophore.

Despite the large literature relating to the use of dyes and laser irradiation in the context of treatment of oral cavity tissues, there remains a need for effective direct targeting and thermolysis in vivo of the biofilm which would minimize harm to healthy tissues and promote healing.

In view of the foregoing, it would be an advancement in the art to provide new approaches for use in treating periodontal and periimplant disease that addressed the drawbacks of the approaches presently available. In particular, it would be an advancement to provide approaches for the treatment of bacterial fueled inflammatory diseases by effectively targeting and destroying the whole live biofilm (and consequently the bacteria) in the three dimensional periodontal/periimplant space, without harming the healthy dental or other tissues. In particular it would be an advancement to provide novel methods for treating a diseased tissue exploiting optical and thermal emissions of near-infrared diode laser systems and fibers in order to target chromophore stained biofilm while minimizing damage to healthy tissues. Furthermore, it would be a desirable advancement to identify methods and means for targeting disease tissue with increased specificity as evidenced by a better control of the coagulation zone of incision with reduced deeper effects.

SUMMARY OF THE INVENTION

The present invention provides a novel approach and compositions (including kits) to expand the therapeutic window of opportunity currently available with conventional dental solid state diode and Nd:YAG lasers in the near infrared spectrum to coagulate live biofilm and kill bacteria thermally without harming the healthy dental structures and tissues of the patient.

To accomplish biofilm coagulation and bacterial thermolysis with a laser (e.g., a dental diode or Nd:YAG laser), there is a small therapeutic window of opportunity available to eliminate the live biofilm and oral pathogenic bacteria from periodontal and periimplant sites. This is accomplished as the optical energy from the laser is converted to local thermal energy in the target site and tissue. Because this therapeutic window is so small, a method is presented to expand the range of the dental diode and Nd:YAG laser to make live biofilm coagulation and bacterial elimination through the thermal deposition of energy a safer and more predictable process. The present invention uses localized delivery of targeting chromophore for the live biofilm in the periodontal or periimplant site. This allows the two parameters, of (1) energy output of the laser and (2) time of laser application, to be lowered to accomplish the tasks of live biofilm coagulation and subsequent bacterial thermolysis in a safer environment.

BRIEF DESCRIPTION OF DRAWINGS

For a fuller understanding of the nature and objects of the present invention, reference is made to the following specification, which is to be taken in connection with the accompanying drawings wherein.

DETAILED DESCRIPTION

The present invention capitalizes on the discovery that significant and factual quantum interactions occur with the distal end of near-infrared laser delivery optical fibers, when the tip of the optical fiber of a near-infrared diode or Nd:YAG laser comes into contact with periodontal/periimplant tissues and instantly becomes a carbonized "hot tip". These quantum and thermodynamic realities are exploited to achieve targeted live biofilm thermolysis using near-infrared lasers and the secondary quantum emissions from the optical fiber (delivery tips) used according to the invention.

Figure 1:
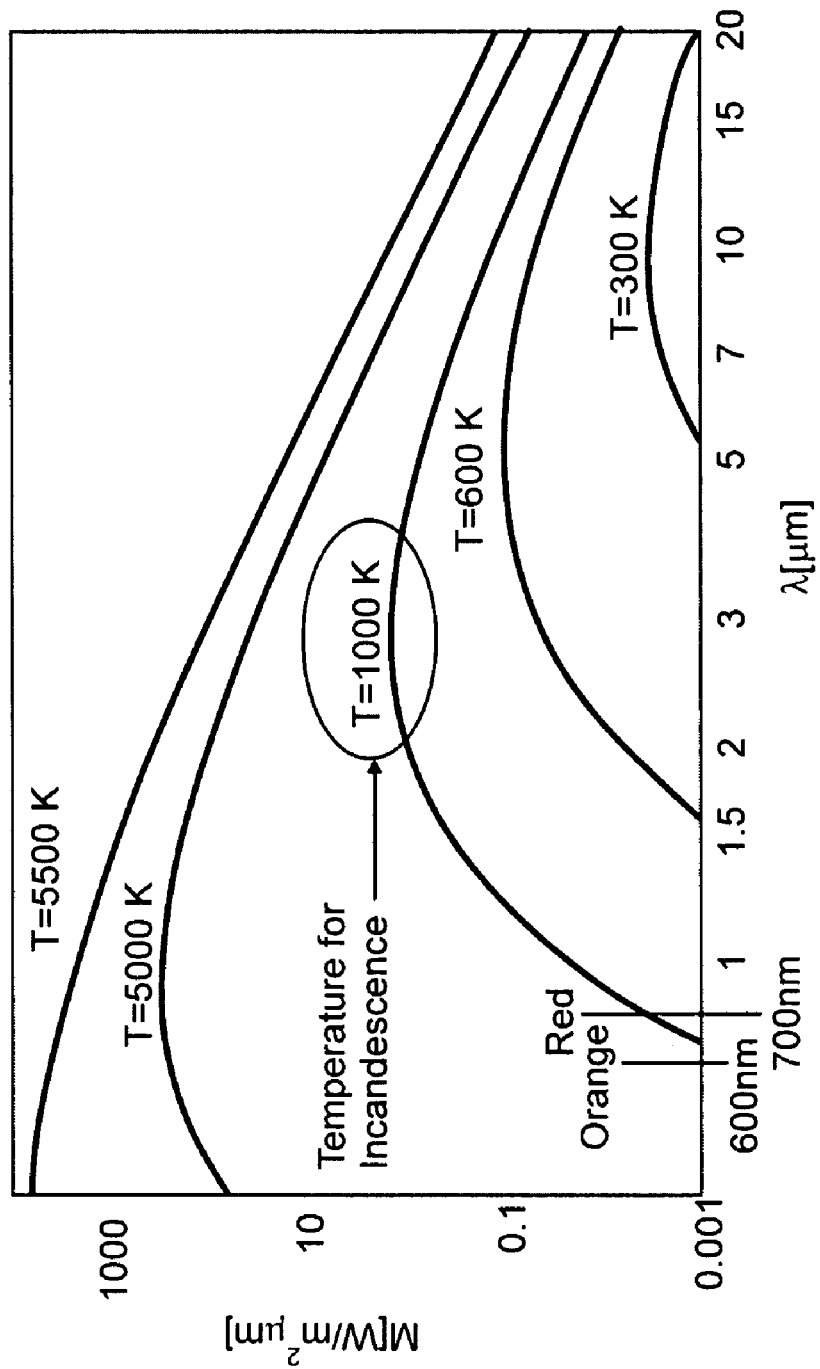
FIG. 1 is a graph illustrating the spectral radiant exitance of a blackbody radiator at different temperatures. On the ordinate (y axis) are shown various optical densities and on the abscissa (x axis) are shown various wavelengths.

The inventor has devised inter alia novel contact "hot tip" techniques exploiting the instantaneous transformation of the laser optical fibers (e.g., the silica fibers) in the delivery device of conventional near-infrared diode or Nd:YAG lasers into incandescent blackbody radiators capable of cutting and vaporizing tissues (see FIG. 1 showing the spectral radiance of a blackbody radiator at different temperatures). Such incandescent blackbody radiators have been found to have quantum and thermodynamic properties useful for the treatment of diseased periodontal and/or periimplant tissues and specifically for the reduction of live biofilm.

Figure 6:
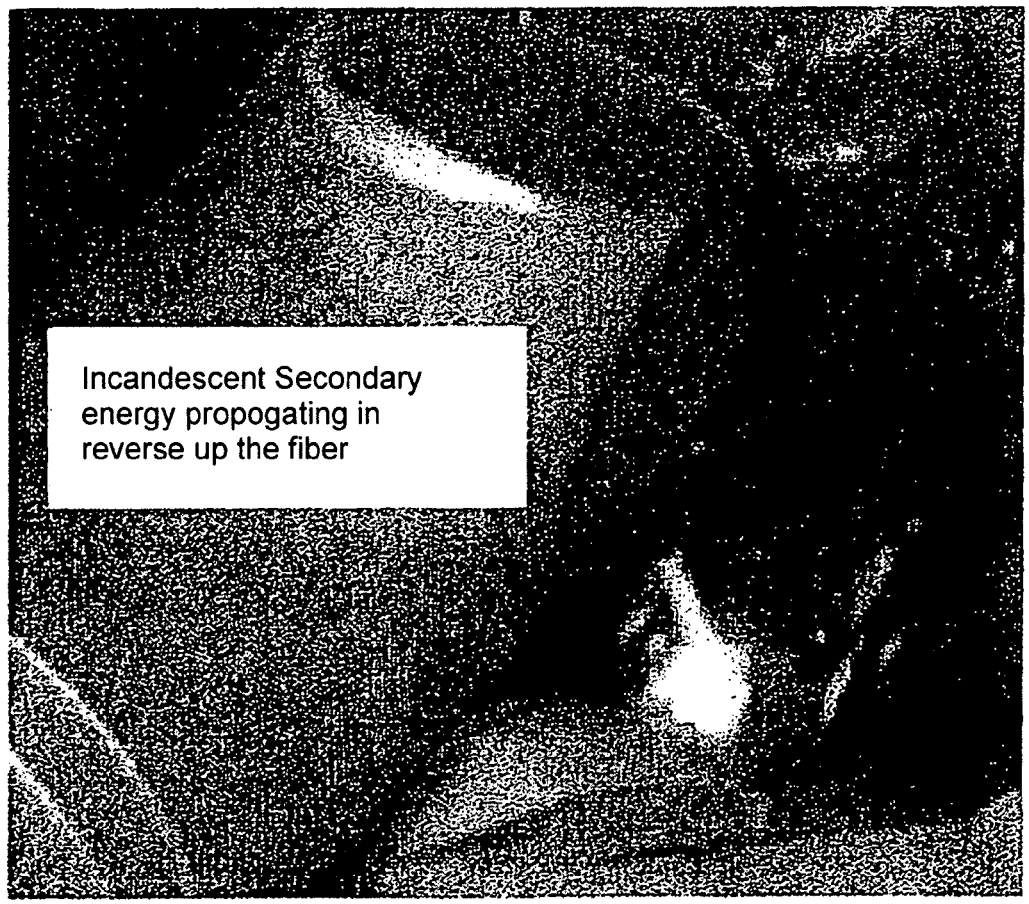
FIG. 6 is a photograph showing the optical fiber now converted to the "hot tip" of the invention identifiable as an incandescence.

When an unclad optical fiber tip emitting photons (FIG. 3A) to a target tissue comes in contact with a live biofilm, or other biological matter such as blood, it will immediately accumulate debris that "stick" to the fiber itself. This debris has been found to immediately absorb the intense near-infrared laser energy propagating through the optical fiber thereby causing an increase in temperature and carbonization of the same (hence the term "hot tip" henceforth designating the blackbody incandescent tip and the carbonized coagulum). The temperature escalates as the energy from the infrared laser photons continues to bombard (and be absorbed by) the newly carbonized hot tip. Upon its conversion to a blackbody radiator (and as it becomes incandescent and it glows, see FIG. 3B), the optical fiber generates a secondary visible optical emission (see FIG. 6).

As used in this specification, the singular forms "a," "an" and "the" specifically also encompass the plural forms of the terms to which they refer, unless the content clearly dictates otherwise. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a method, the term "comprising" means that the process includes at least the recited steps, but may include additional steps. When used in the context of a composition, formulation or a kit the term "comprising" means that the compound or composition includes at least the recited features or components, but may also include additional features or components.

The methods and compositions according to the invention thus combine the primary emissions of conventional near-infrared diode or Nd:YAG lasers with the secondary quantum emissions from the optical laser used according to the invention for the treatment of chromophore-stained periodontal or periimplant tissue to target live biofilm thus treating periodontal disease in a tissue (e.g., in the oral cavity). One of skill will appreciate that while the invention is exemplified in the dental field, it may be applied in many other fields targeting infections in virtually any tissue. Hence, for example the tissue could be the hip, where irrigation with a chromophore (e.g., 1% Methylene Blue solution) and the subsequent use of a laser according to the invention will coagulate the targeted infection in that area of the body. Furthermore, while the invention is exemplified in human patients, the methods and compositions of the present invention are intended for use with any mammal that may experience the benefits of the method and composition of the invention. Foremost among such mammals are humans, although the invention is not intended to be so limited, and is also applicable to veterinary uses. Thus, in accordance with the invention, "mammals," or "mammal in need," or "patient" include humans as well as non-human mammals, particularly domesticated animals including, without limitation, cats, dogs, and horses.

A large number of laser sources in the infrared spectrum have been used to kill pathogenic bacteria in dentistry and medicine. For the last few years near infrared solid state diode and Nd:YAG lasers have been used in the field of dentistry for tissue cutting, cautery, and bacterial thermolysis. The four most widely used dental near infrared wavelengths are 810 nm, 830 nm, 980 nm and 1064 nm. These near infrared lasers have very low absorption curve in water, and have a very deep tissue penetration values as detailed infra.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art.

An aspect of the invention provides novel methods for the treatment of periodontal disease in a periodontal or periimplant tissue of a patient having periodontal disease. The tissue being treated by the methods of the invention is contracted with a heat sink moiety including at least a dye absorbing at a predetermined spectral range. A "heat sink" moiety is any entity capable of receiving, absorbing, or otherwise diverting heat from the tissue being irradiated. Heat sink moieties according to the invention include compounds known to act as chromophore dyes (i.e., molecules that preferentially absorb optical energy). The term "predetermined spectral range" is from about 400 nm to about 1100 nm. In certain embodiments, the chromophore dye has absorption bands (and thus a predetermined spectral range of) from about 600 to about 700 nm. A heat sink moiety needs to be essentially non-toxic to tissues, needs to be able to penetrate live biofilm, and—most important—needs to be selectively absorbed by the live biofilm to target the same without damaging the patient tissues. Representative non-limiting examples of chromophore dyes include Toludine Blue (with absorption spectra between 600 to 700 nm), Methylene Blue (MB, with absorption peaks at 609 (orange) and 668 nm (red)), Congo Red (with strong absorption band at 340 nm in the near-ultraviolet region and another at 500 nm near the blue-green transition region), and Malachite Green (with a strong absorption band centered at 600 nm near the yellow-red transition region, and any other tissue safe biological dye). One of skill will appreciate that chromophore dyes may be administered in a composition form including any known pharmacologically acceptable vehicle with any of the well known pharmaceutically acceptable carriers, including diluents and excipients (see *Remington's Pharmaceutical Sciences*, 18th Ed., Gennaro, Mack Publishing Co., Easton, Pa. 1990 and *Remington: The Science and Practice of Pharmacy*, Lippincott, Williams & Wilkins, 1995).

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

According to the methods of the invention, the periodontal/periimplant tissue stained with the chromophore dye (composition) is irradiated with optical energy in the near infrared spectral range.

Figure 4:
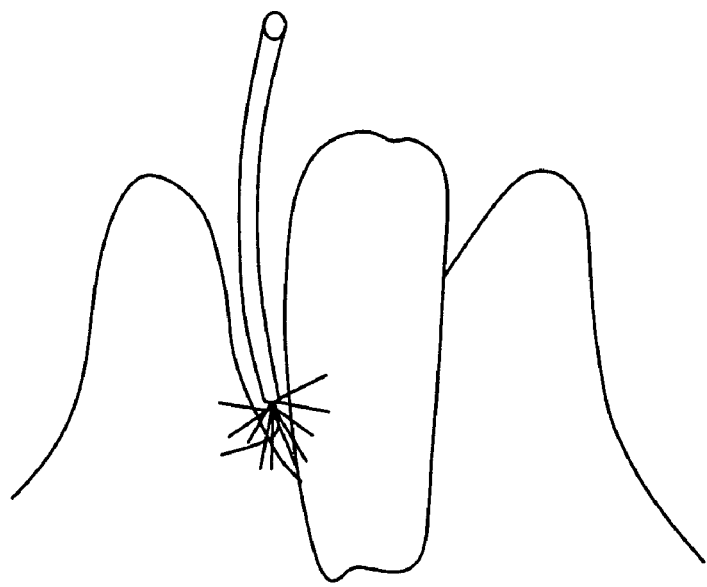
FIG. 4. is a diagram illustrating the optical fiber now converted to an incandescent blackbody radiator (the "hot tip" of the invention) in contact with the tissue being treated (i.e., the periodontal pocket).

The skilled practitioner will realize that the instant invention combining live biofilm chromophore targeting and thermolysis, may be used to augment traditional approaches by promoting healing upon removal of the live biofilm. Accordingly, the methods and compositions of the invention could be used to target the live biofilm in the periodontal or periimplant pocket (see FIG. 4) followed by mechanical debridement of the denatured biofilm (now reduced to a denatured and inactive solid coagulum entrapping live and dead bacteria within their matrix in the periodontal or periimplant pocket) and its constituent flora. By this approach, the periodontal/periimplant instruments (e.g., periodontal scalers or ultrasonic scalers) are able to scale and debride the denatured biofilm out of the local area with much greater success than would be possible if the slimy live biofilm remained uncoagulated. Live biofilm chromophore targeting thus, achieves the goals of traditional bacterial removal by traditional scaling and mechanical debridement. Moreover, it seeks out and target previously inaccessible areas for periodontal/periimplant pocket treatment and concurrently kills and removes the living biofilm as a denatured inactive solid coagulum.

Similarly, the instant methods and compositions may be combined with traditional approaches involving antibacterial modalities found in the literature such as for example antibiotic treatment (for a standard reference works setting forth the general principles of pharmacology see, Goodman and Gilman's *The Pharmacological Basis of Therapeutics*, 10$^{th}$ Ed., McGraw Hill Companies Inc., New York (2001); for a general reference relating to the use of antibiotics in dentistry see for example, Rose et al., *Periodontics: Medicine, Surgery, and Implants*, June 2004 in concomitance with or following laser treatment. Hence, as exemplified hereinafter (see Example 2) a patient may be treated with a penicillin to prevent reinfection. Such combinations may be effected prior to, in conjunction with, and/or following laser treatment (irradiation). Hence, formulations of compositions according to the invention may contain more than one type of chromophore dye according to the invention, as well any other pharmacologically active ingredient useful for the treatment of the symptom/condition being treated. Hence, in some instances the practitioner may opt to co-administer other active or inactive components including, but not limited to, antibiotics, analgesics, and anesthetics. Examples of useful antibiotic or antimicrobial agents include, but are not limited to, chlorhexidine gluconate, triclosan, cetyl pyridinium chloride, cetyl pyridinium bromide, benzalkonium chloride, tetracycline, methyl benzoate, and propyl benzoate. Examples of useful anesthetic agents include, but are not limited to, benzocaine, lidocaine, tetracaine, butacaine, dyclonine, pramoxine, dibucaine, cocaine, and hydrochlorides of the foregoing.

As used herein, by "treating" is meant reducing, preventing, and/or reversing the symptoms in the patient being treated according to the invention, as compared to the symptoms of an individual not being treated according to the invention. A practitioner will appreciate that the compounds, compositions, and methods described herein are to be used in concomitance with continuous clinical evaluations by a skilled practitioner (physician or veterinarian) to determine subsequent therapy. Hence, following treatment the practitioners will evaluate any improvement in the treatment of the disease according to standard methodologies. Such evaluation will aid and inform in evaluating whether to increase, reduce or continue a particular treatment dose, mode of administration, etc.

Live biofilm targeting and secondary emission coagulation of the biofilm can be accomplished without harming collateral tissues, healthy periodontal/periimplant architecture or the tooth. Further, this can be accomplished without (necessarily) introducing antibiotics or resorbable delivery vectors into the system or periodontal pocket, and will allow for the immediate healing and reattachment of periodontal tissues to begin.

The bacteria targeted in accordance with the present invention are those specifically involved in art-known periodontal and periimplant infections (e.g., *Actinobacillis actinomycetemcomitans, Porphyromonas gingivalis, Prevotella intermedia/nigrescens, Bacteroidesforsythus, Fusobacterium* species, *Peptostreptococcus micros, Eubacterium* species, *Camplobacter rectus, streptococci,* and *Candida* species). Also contemplated are art-known periimplant infectious bacteria (e.g., *Fusobacterium* spp., *Prevotella intermedia, Porphyromonas gingivalis, Actinobacillus actinomycetemcomitans, Peptostreptoccus micros, Bacteroides* spp., *Capnocytophaga* spp., *Prevotella* spp., *Spriochetes, Staphylococcus* spp., Enteric gram-negative bacteria, *Campylobacter gracilis, Streptoccus intermedius, Streptococcuc constellatus, Candida albicans,* and *Eikenella corrodens*).

The energy may be provided by any suitable source of coherent energy, e.g., a laser, capable of emitting optical energy having a wavelength from about 500 to about 1500 nm, if necessary or convenient using optical fibers or other known optical devices to deliver the energy to the periodontal and/or the periimplant being treated. In certain embodiments, the optical energy generated is coherent energy (e.g., generated by a laser such as a diode laser or a Nd:YAG laser operating at 350-1200 mW, preferably at 500-1200 mW, or at 800-1200 mW). Thus, lasers according to the invention include those emitting optical energy having a wavelength of from about 500 to about 1500 nm, preferably from about 600 to 1100 nm, or from about 800 to about 1100 nm. In representative non-limiting examples shown herein the wavelength is from about 800 to about 1064 nm.

There are generally five factors to consider regarding heat generation by the primary emissions of near infrared lasers when the distal end of the laser fiber is clean and well cleaved (as a general reference, see Niemz M, *Laser-Tissue Interactions. Fundamentals and Applications*, Berlin, Springer, pp 45-80, 2002)). These factors are: (1) wavelength and optical penetration depth of the laser; (2) absorption characteristics of exposed tissue; (3) temporal mode (pulsed or continuous); (4) exposure time; and (5) power density of the laser beam.

Diode lasers in the near infrared range have a very low absorption coefficient in water, hence they achieve deep optical penetration in tissues that contain 80% water (including the oral mucosa, bone and gingiva). This means that for a conventional dental diode soft tissue laser the depth of penetration per pulse is estimated by Niemz to be about 4 cm. The shorter wavelengths of the near-infrared diode and Nd:YAG lasers have very high absorption peaks in molecules (chromophores) such as melanin and hemoglobin. This will allow the laser energy to pass with minimal absorption through water, producing thermal effects much deeper in the tissue (as photons are absorbed by the deeper tissue pigments). This photobiology allows for controlled deeper soft-tissue coagulation, as the photons that emerge (in a cone pattern of energy) from the distal end of a clean cleaved near-infrared diode laser fiber, are absorbed by blood and other tissue pigments.

The next parameter to bear in mind is the heat effect on the tissue being irradiated, based on the pulse mode of currently available near-infrared systems. Presently, for periodontal treatment, near-infrared lasers either emit photons in the Continuous Wave (CW) or Gated CW Pulsed Mode for Diode systems, and Free Running Pulsed (FRP) for Nd:YAG's. Thus, because the length (duration) of the tissue exposure to the photon energy of the laser will govern the thermal tissue interaction that is achieved.

In the CW or Gated CW mode, laser photons are emitted at one single power level, in a continuous stream. When the stream is Gated, there is an intermittent shuttering of the beam, as a mechanical gate is positioned in the path of the beam, essentially turning the laser energy on and off. The duration of on and off times, of this type of laser system is generally on the order of milliseconds (1 millisecond=1/1000th of a second), and the "power-per-pulse" stays at the average power of the CW beam. Nd:YAG lasers (in the FRP mode) can produce very large peak energies of laser energy, for extremely short time intervals on the order of microseconds (1 microsecond=1/1,000,000th sec). As an example, one of these lasers with a temporal pulse duration of 100 microseconds, with pulses delivered at ten per second (10 Hz), would mean that the laser photons are hitting the tissue for only 1/1000th of a second (total time) and the laser is "off" for the remainder of that second. This will give the tissue significant time to cool before the next pulse of laser energy is emitted. These longer intervals between pulses will benefit the thermal relaxation time of the tissue. The CW mode of operation will always generate more heat than a pulsed energy application.

If the temporal pulses are too long (or the exposure in CW is too long), the thermal relaxation effect in the tissues is overcome and irreversible damage to non-target areas can occur. An added safety feature is provided by the Methylene Blue acting as a "heat sink" around vital tissues providing a larger margin of error cooling and appropriate exposure times are miscalculated. So, not only the ultimate temperature reached in the tissue interaction with the laser energy is of concern, but also the temporal duration of this temperature increase plays a significant role for the induction of desired tissued effects, and the inhibition of irreversible tissue damage. For nano- and pico-second pulses, heat diffusion during the laser pulse would be negligible, however presently available dental lasers cannot achieve such pulses.

The power density of the beam is determined by the peak power generated by the laser, divided by the area of the focused beam. This means that the smaller the diameter of the fiber used to deliver the energy (200 μm, 400 μm, 600 μm), and the closer the fiber is to the tissue (i.e., a smaller "spot size", not touching the tissue), the greater the power density (amount of emitted photons per square mm of the beam) and the greater the thermal interaction. With a non-contact "clean" fiber tip, the two most important considerations are the spot size of the beam, and the distance of the fiber tip to the tissue.

There is an immediate and profound change in the quantum emissions of the laser fiber, and an immediate and profound change in the tissue response and photobiology when an unclad "naked' fiber tip comes in contact with periodontal and/or periimplant tissue at any fluence above about 300 mW continuous output. This occurs in 100% of all intrasulcular periodontal procedures using simple naked unclad fibers, regardless of the diode laser or Nd:YAG wavelength from approximately 600 nm to 1100 nm. When an unclad "naked" fiber tip comes in contact with periodontal tissue and intra-sulcular fluids, cellular debris and biofilm will immediately accumulate on the unclad tip, and this debris will instantly absorb the intense infrared laser energy propagating through the fiber, which will cause the tip to heat and immediately carbonize. As the energy from the infrared laser photons continues to be absorbed by this newly carbonized tip, (within as short a time as a single second) the tip will become red hot (above 726° C.). This resulting secondary quantum emission of the "hot tip" energy to the tissue is associated with different heat transfer and photobiologic events in the periodontal pocket and periodontal tissues. That is the primary focus of this invention. This allows the two parameters, of (1) energy output of the laser and (2) time of laser application, to be lowered to accomplish the tasks of live biofilm coagulation and subsequent bacterial thermolysis in a safer environment.

By direct live biofilm chromophore targeting, and for the first time exploiting the inherent secondary quantum emissions with this hot tip technique and the chromophore Methylene Blue, the operator of an 800 nm-1064 nm dental laser can decrease the power of the laser to approximately 0.05-1.5 Watts, and decrease the time needed in the area of treatment. Even with turning down the energies, and treating the area of the periodontal or periimplant pocket for less time than would be necessary without the chromophore heat sink, live biofilm phase change through coagulation and thermolysis of the bacteria within the biofilm will occur. This will lead to a safer procedure for the patient, and preserve more collagen, bone, and mucosa in the periodontal/periimplant pocket from irreversible thermal damage during the procedure.

With the "hot tip" technique the deeply penetrating primary laser energy is substantially reduced, and the photobiology and laser-tissue interaction is different from what is found when using a non-carbonized fiber that emits only the primary emission, near-infrared photons. To accomplish safe and predictable periodontal/periimplant procedures with a "hot tip", the clinician must be mindful of the very narrow therapeutic window afforded by the tip's thermal interactions with the tissue. When radiant optical and thermal energy is applied to biological tissues with a "hot tip", the temperature of the contact area rises immediately. At 45° C., the tissue becomes hyperthermic. At 50° C., there is reduction in cellular enzyme activity and some cell immobility. At 60° C., proteins denature, and there is evidence of coagulation. At 80° C., cell membranes become permeable, and at 100° C., water and tissue begin to vaporize.

If the temperature increases for 2 to 5 seconds beyond 80° C., there will be irreversible damage to the mucosa, bone, periodontal, and dental structures. These considerations are of direct importance for contact tip procedures such as a gingivectomy, gingivoplasty, frenectomy, incision and drainage, removal of a fibroma, and periodontal sulcular currettage (see Rossman, J. Periodontol. 73:1231-1239 (2002)).

According to the invention, the optical fiber emitting optical energy in the near infrared spectral range is contacted with at least a portion of the tissue previously stained with the chromophore dye. According to the invention, the tissue should be irradiated for a therapeutically effective amount of time in a moving pattern. The expression "therapeutically effective amount of time" and "therapeutically effective time window" is used to denote treatments for periods of time effective to achieve the therapeutic result sought. Because of the immediacy of the result sought (i.e., the formation of the coagulum from the biofilm) the practitioner is able to tailor and ascertain therapeutically effective times visually. The invention therefore provides a method to tailor the administration/treatment to the particular exigencies specific to a given patient. As illustrated in the following examples, therapeutically effective amounts may be easily determined for example empirically by starting with a relative short time period and by step-wise increments with concurrent evaluation of beneficial effects.

Prior to the invention, the objective when using a laser with a "hot tip" in the periodontal pocket, was to generate sufficient thermal energy at the tip to cause immediate tissue vaporization and ablation limited to the inflamed epithelial periodontal lining, otherwise known as sulcular curettage. To accomplish it, the tissue must be rapidly heated to several hundred degrees Celsius at the contact point of the tip. A diode or Nd:YAG laser can readily accomplish this when used in the contact mode. As the optical and thermal energy (of the secondary blackbody emission) is directly transferred to the tissue in the vicinity of the tip, a poorly controlled vaporization of sulcular epithelium ensues.

During these procedures, it is imperative to keep treatment contact intervals in any one spot relatively short (1 second), since any extra exposure of periodontal tissues (including tooth and bone) the tip will damage these peripheral tissues. The will occur because the heat will be transferred deeper into the tissues via heat conduction, and will not be rapidly dissipated by the tissues if there are any prolonged periods of contact. If the contact exposure time is too long (more than 2-3 seconds in one area), the ability of the tissues to dissipate heat is overcome, and irreversible damage occurs to non-target tissues.

As stated, in the contact mode a large percentage of the near-infrared photons (the primary emission of the laser) are absorbed by the blackbody tip and carbonized coagulum. As a result, the emission, and hence penetration and absorption of these primary (single wavelength) infrared photons generated from the laser, are greatly decreased. Therefore, the danger to peripheral tissues (around the periodontal pocket) is directly dependent on the exposure time of the "hot tip" to the tissue and the heat conduction from the tip to the tissue. These greatly decreased primary emissions of the laser through a carbonized tip were studied in detail by Grant et al., Lasers in Surgery and Medicine 21:65-71 (1997), as they specifically looked at the "fiber interaction" during contact laser surgery. Grant showed that with tissue deposits at the tip of the fiber absorbing larger amounts of laser light, immediate carbonization occurs. The carbonization of the fiber tip leads to an increase in temperature, and this can result in significant damage to the optical quality of the fiber (the temperature spikes to greater than 900° C.). Grant also found that once the carbonization of the tip occurs, the tip no longer functions as an adequate forward light guide (i.e., there is now limited primary photon forward progression of laser energy). The laser will no longer adequately photocoagulate, but rather it incises and cauterizes the tissue because of the intense heat at the tip. While the hot tip described in Grant et al. has direct and unimpeded energy effecting the tissues within the sulcus, the current invention's hot tip is exploited by making it possible to coagulate the target biofilm in total (because of the heat sink/chromophore), while at the same time the peripheral tissues are left protected.

It is also important to remember that the silica portion of a typical optical fiber consists of two regions—the core that runs through the center of the strand, and the cladding that surrounds the core. The cladding has a different refractive index than the core, and acts as a mirror that causes the laser light to reflect back into the core during its transmission through the fiber. Furthermore, longer lasing times and higher power drastically reduce the forward power transmission of the laser light, as the fiber tip sustains more and more heat induced damage. When a 360 micron fiber (with a 830 nm diode laser at 3 watts CW, with a laser power meter) was tested, it was found that an immediate 30% loss of forward power transmission is observed with fiber carbonization from tissue detritus. Further power loss was observed as lasing time continued and tissue debris accumulated.

Willems et al., Lasers in Surgery and Medicine 28(4):324-329 (2001) elucidated this phenomenon in vivo using diode and Nd:YAG lasers. Conventional fiber tips and coated fiber tips were compared for ablation efficiency in rabbit cerebral tissue. With the conventional fiber tips, histology and thermal imaging demonstrated deleterious effects deep into the tissue. When using the coated fiber tip, they reported that almost all laser light was transformed into thermal energy (as the tip carbonized), and instantly produced ablative temperatures at the tip itself. Further, they reported that ablation was observed at relatively low energy and power (1 W for 1 second) with thermal effects restricted only to the superficial structures. This restriction of thermal effects to superficial structures can be explained, as the forward power transmission of the laser light is attenuated when a larger percentage of the primary emissions of the laser are absorbed by the tip. As a result, the optical transmission qualities are damaged. In order to protect deeper tissues, they altered the distal end of the tip to completely inhibit any forward progression of primary infrared photons, whereas the present invention utilizes a chromophore/heat sink to both target the biofilm and protect the surrounding tissues. Also of significance, as the quality of the fiber transmission diminishes as a result of damage to the tip, the energy, focus, and homogeneity of the energy being transmitted from the tip is affected. The primary energy that is still available for forward power transmission out of the tip is far less efficient for tissue penetration and photocoagulation. This inventor has developed a novel system to exploit these quantum realities, with biofilm targeting technology.

Furthermore, (Proebstle et al., Dermatol. Surg. 28:596-600 (2002)) in a study evaluating the thermal damage to the interior walls of veins with 600 μm fibers in endovenous laser treatment, found no major differences could be detected between the three diode laser wavelengths of 810 nm, 940 nm, and 980 nm. The laser wavelength interaction with the blood immediately transferred the optical energy completely into heat at all wavelengths, even with new, uncarbonized fibers. In essence, what Proebstle's data confirms, is that when delivery tip carbonization occurs (now understood to be a universal event with these lasers), and tip preferentially absorbed the laser energy causing extremely high temperature generation and a "hot tip" (all intra-pocket periodontal and periimplant procedures) any subtle wavelength differences in the near infrared 800-1100 nm are not critical to the procedure being performed.

It is now understood that optical fiber tips used with near infrared lasers (600 nm-1100 nm) at moderate fluences (about 350 mw and above) experience heat induced carbonization almost immediately upon contact with oral tissues and/or blood. The carbonization is thermally driven, and causes degradation of the forward power transmission potential from the tip, as the tip absorbs the primary infrared photons from the laser and becomes red hot and incandescent. Upon carbonization, this tip can be referred to as a blackbody emitter of secondary radiation (ultraviolet, visible, and infrared light), and has a thermal interaction and photobiology distinctly different from what occurs with clean, uncarbonized non-contact fibers. It is no longer single primary emitter of monochromatic laser energy.

With all visible and infrared light, after the energy of the photons is absorbed by a chrompohore, it is converted to kinetic energy within the target molecules (i.e., heat). The energy transferred may cause damage (e.g., excessive dosimetry). It has been found that a heat sink is ideally suited in conjunction with near infrared laser periodontal treatment with secondary quantum emissions generated from a "hot tip" blackbody radiator. Heat deposition may be due to local conversion of optical energy from the laser in the tissue to heat energy, or to heat conduction from the hot-tip (quantum secondary blackbody emissions) of the naked or unclad optical silicate delivery fiber within the periodontal or periimplant pocket.

With these thermodynamic realities now understood, it is easily explained that excess power output from the laser, or excess time in a dental surgical procedure can induce heat related deleterious effects to the patient and irradiated tissues.

To accomplish safe and predictable periodontal therapy (and biofilm coagulation with bacterial cell death) with near infrared dental diode lasers, the operator must be cognizant of the very narrow therapeutic window afforded by the lasers thermal interactions with human tissues.

To achieve photothermolysis (heat induced death) and live biofilm coagulation with the near infrared dental laser, a significant temperature increase must occur for a given amount of time in the target tissue or tissue area of the periodontal pocket. From 60° C. to 80° C. is the range of temperature in the surrounding tissue that must be achieved for short periods of time, under skilled control and delivery, for the live biofilm phase shift to occur, and transform from a slimy proteinacious matrix to a solid coagulum. This must occur for the near infrared dental laser to be effective at biofilm thermolysis without causing undue harm to healthy oral tissues.

Figure 2:
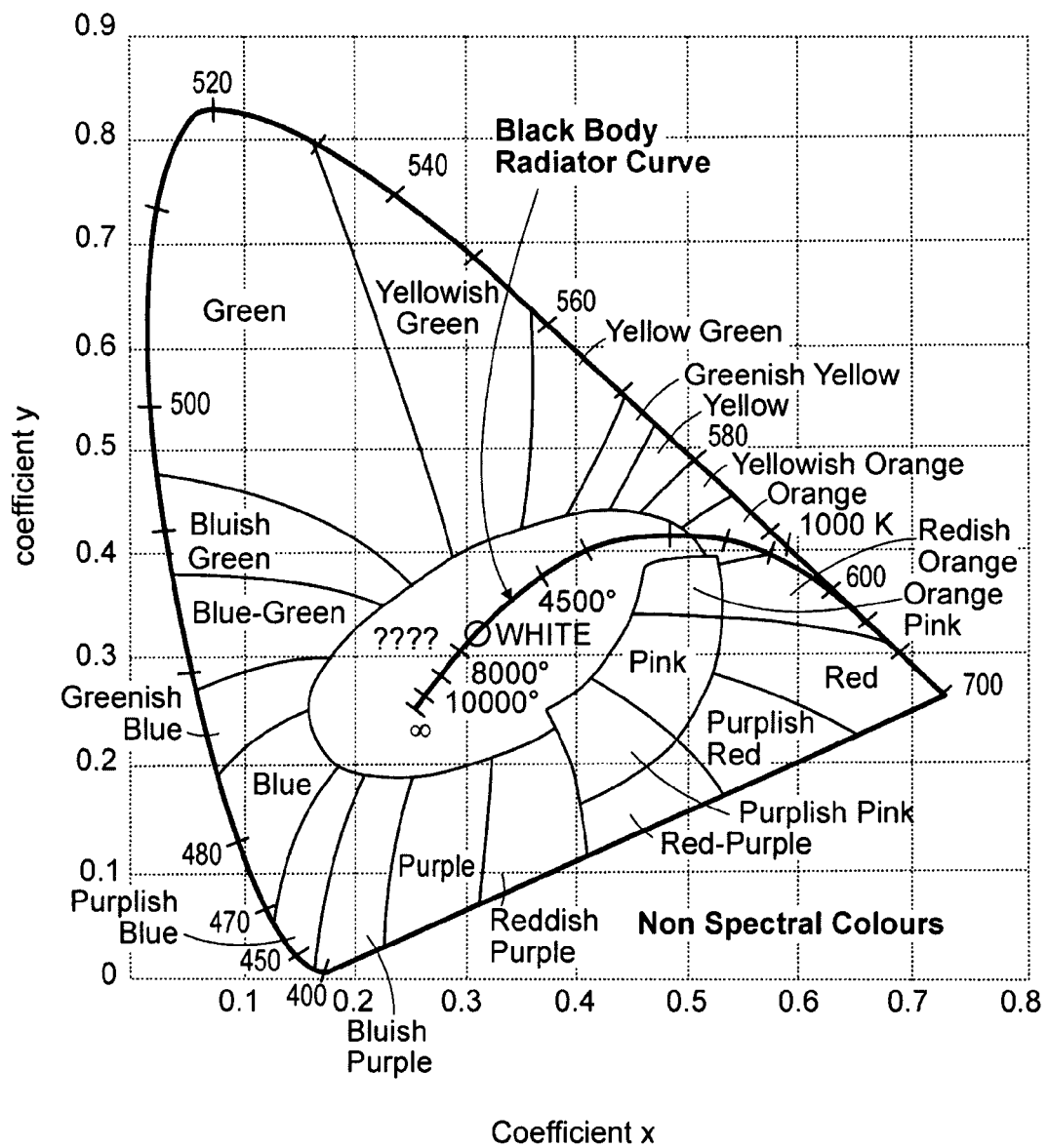
FIG. 2 is a diagram illustrating a chromaticity map for a representative chromophore dye according to the invention: Methylene Blue.

As the tip begins to glow (i.e., as it becomes a "hot tip"), it emits first red, and then orange visible light as is evidenced by a C.I.E. Chromaticity Map that is overlaid with a blackbody locus (FIG. 2) (in the 600 nm to 700 nm range). This emission falls exactly within the absorption band for Methylene Blue. Thus the biofilm stained therewith selectively absorb the energy emitted by the hot tip.

The invention provides a kit for treating an in vivo biofilm and tissue on a periodontal or periimplant surface including an optical fiber extending between a proximal end and a distal end. According to the invention, the proximal end receives optical energy incident thereon in a near infrared spectral range, and the optical fiber transmits the received optical energy to the distal end emitting optical energy in the predetermined spectral range. The terms and specific features of the elements in the kits of the invention are as described above in connection with the methods of the invention. In certain embodiments, the predetermined spectral range is from about 600 to about 700 nm.

The distal end of the optical fiber may be made of silica, zircon glass or other compatible material capable of generating a "hot tip" (e.g., fused silica). For each different procedure and patient, the old blackbody tip is cleaved off and the fiber sterilized to prepare the fiber for a new patient.

Figure 5:
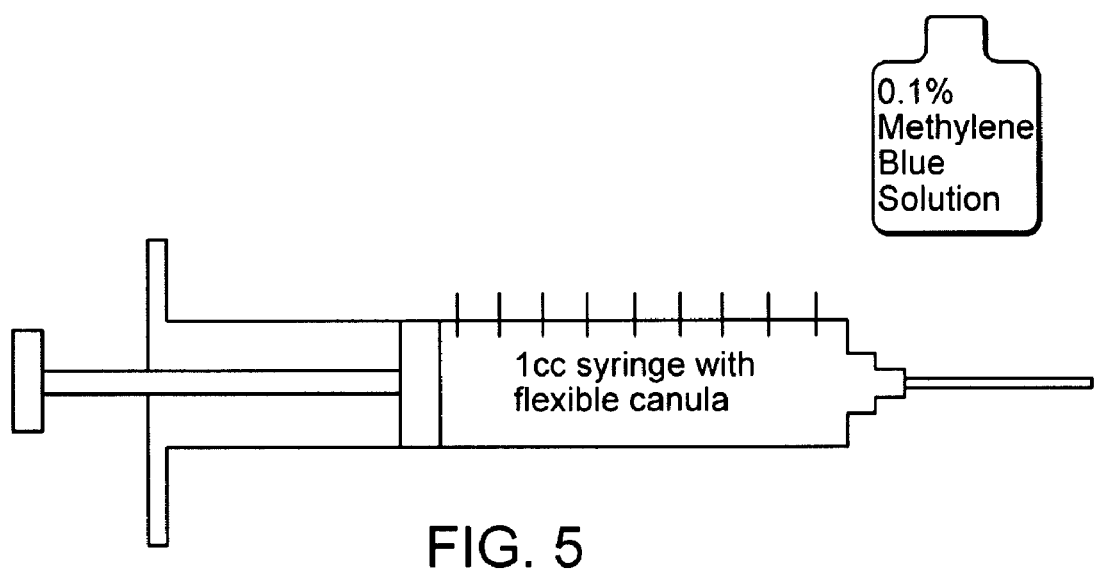
FIG. 5 is a diagram illustrating a syringe as an example of a delivery system for the delivery of Methylene Blue to the periodontal or periimplant pocket by use of a syringe.

Kits according to the invention further include a reservoir to store a chromophore dye having an absorption spectrum in the spectral range of a blackbody radiator described herein the invention. In certain embodiments, the reservoir includes an applicator assembly for the selective application of the chromophore dye to the biofilm and tissue on the periodontal or periimplant surface (such as for example a small fiber brush, or a syringe, see FIG. 5 exemplifying a syringe and a reservoir containing a 0.1% MB solution).

Kits according to the invention may further comprise an optical energy source for generating optical energy in the near infrared spectrum, and an associated coupling assembly for coupling the optical energy to the proximal end of an optical fiber. In certain embodiments, the optical energy generated is coherent. In other embodiments, the optical energy source is a diode laser operating at 350-1200 mW generating energy having a wavelength of about 830 nm.

The kits according to this aspect of the invention may also include heat sink moieties as discussed infra. Accordingly, some kits include a chromophore dye such as MB. The heat sink moieties of the invention may be provided in a reservoir adapted to store a chromophore dye characterized by an absorption spectrum in the spectral range of a blackbody radiator described herein the invention. The reservoir may further include an applicator assembly adapted to effect selective application of the chromophore dye to a region of the biofilm on a periodontal or periimplant surface. The chromophore dye may be pre-packed in a reservoir with a light foil cover. In some embodiments, the practitioner pushes on the brush, breaks the foil, and wets the bristles with the dye (e.g., MB) for topical deposition to the area of the oral cavity to be treated. These areas include the periodontal pocket, the periimplant site, and or any other site in the oral cavity requiring treatment according to the invention.

Figure 3A:
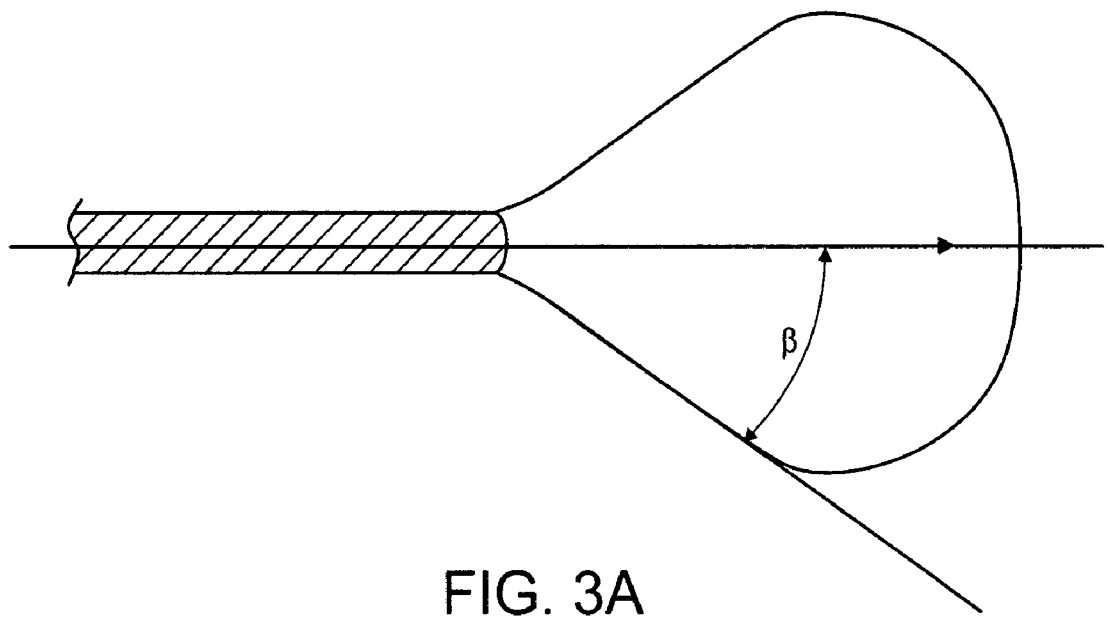
FIG. 3A is a diagram illustrating a clean cleaved optical fiber tip before blackbody reaction according to the invention.
Figure 3B:
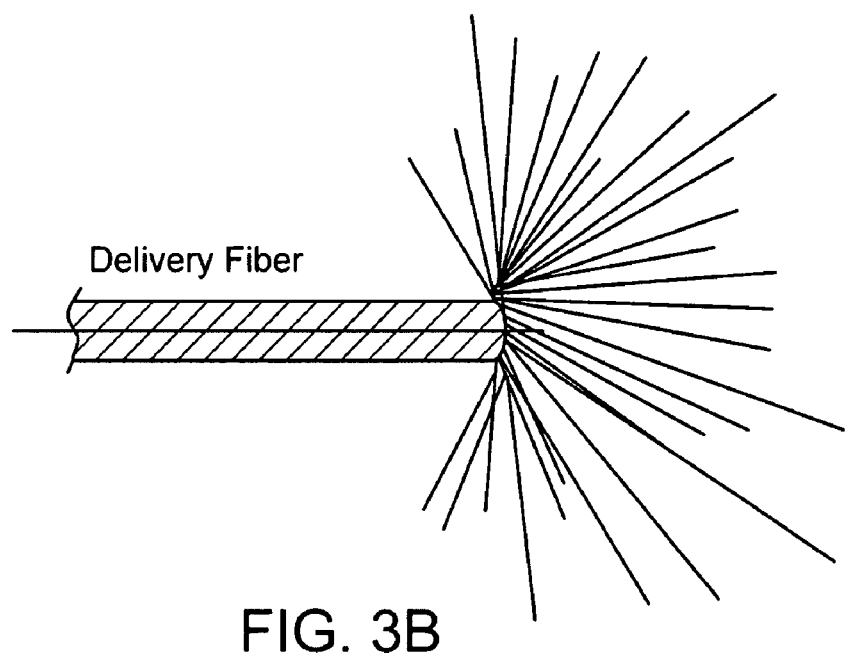
FIG. 3B is a diagram illustrating the secondary optical and thermal energy generated from a carbonized laser delivery fiber according to the invention.

The laser energy may be delivered through a commercially available surgical fiber from 200 microns to 1000 microns in diameter with an unclad and cleaved distal end, in contact or non-contact mode (FIG. 3A). The laser energy is delivered from a solid state continuous wave or pulsed dental diode or Nd:YAG laser ranging from 800 nm to 1064 nm to make use of the secondary emission blackbody reaction with the hot tip and the absorption peak in MB. The laser energy is delivered from 1 to 120 seconds per area in a moving pattern that never stays stationary for more than 2-3 seconds. The energy production from the laser at the distal end of the conical tip fiber is no less than 200 mW and no more than 4000 mW.

When a lasers output powers (W) and beam area (cm$^2$) are known with a clean cleaved fiber, the remaining parameters of effective treatment can be calculated to allow the precise dosage measurement and delivery of energy for effective and safe treatment to oral tissues. In the periodontal pocket however, with the fiber tip immediately becoming an incandescent blackbody radiator, the normal power equations will not reflect the reality of the new quantum mechanics. Even with the generation of secondary blackbody emissions, the output power of a laser does not change, and simply refers to the number of photons emitted at the given wavelength of the laser.

Before the fiber touches tissue, the power density of the laser will measures the potential thermal effect of laser photons at a treatment irradiation area. Power Density is a function of Laser Output Power and Beam area (again with a clean cleaved fiber), and is calculated with the following equations:

$$\text{Power Density} = (W/cm^2) \qquad (1)$$
$$= \frac{\text{Laser Output Power}}{\text{Beam Diameter}(cm^2)}$$

Hence, the total photonic energy delivered into the oral tissues by a dental near-infrared laser (before the clean tip touches the tissues) is measured in Joules, and is calculated as follows:

$$\text{Total Energy(Joules)} = \text{Laser Output Power(W)} \times \text{Time (Secs)} \qquad (2)$$

Once the tip touches biofilm or tissue and becomes an incandescent blackbody radiator, approximately 70+% of the output power of the laser is converted to local heat, it no longer emits significant monochromatic light (i.e., because the carbonized tip is absorbing it) and it now produces light in a continuous distribution of wavelengths (continuous spectrum) and in all directions. Hence, there is no "spot size" available for a "power density" equation. For this reason, the total energy equation (2), will be used.

In some applications, it may be desirable to broaden or increase the effective surface area from which incandescent light (that falls within the absorption band of the dyed biofilm) is emitted, for example by causing incandescent radiation to be emitted from areas of the optical fiber other than the narrow distal tip alone. In this way, an increased amount of incandescent light may be available to be absorbed by the stained biofilm, at a faster speed, thereby more effectively accomplishing the desired thermolysis of the dyed biofilm in the tissue treated.

In some embodiments, such an increase in the effective surface area from which incandescent light is emitted is accomplished by causing at least some light propagating from the distal tip (toward the proximal end) to be directed onto the dyed biofilm or other target tissue, through the lateral walls of the optical fiber. As explained above, not all of the incandescent radiation (or "secondary quantum emission") that is generated from the carbonized fiber optic tip is transmitted onto the target tissue (e.g. the biofilm stained with Methylene Blue). Rather, some of the incandescent radiation generated from the glowing carbonized tip of the fiber propagates in "reverse" through the fiber optic core, from the distal end toward the proximal end of the optical fiber. In some embodiments, this back-propagating incandescent radiation can be directed onto target tissue, as described below.

Figure 7:
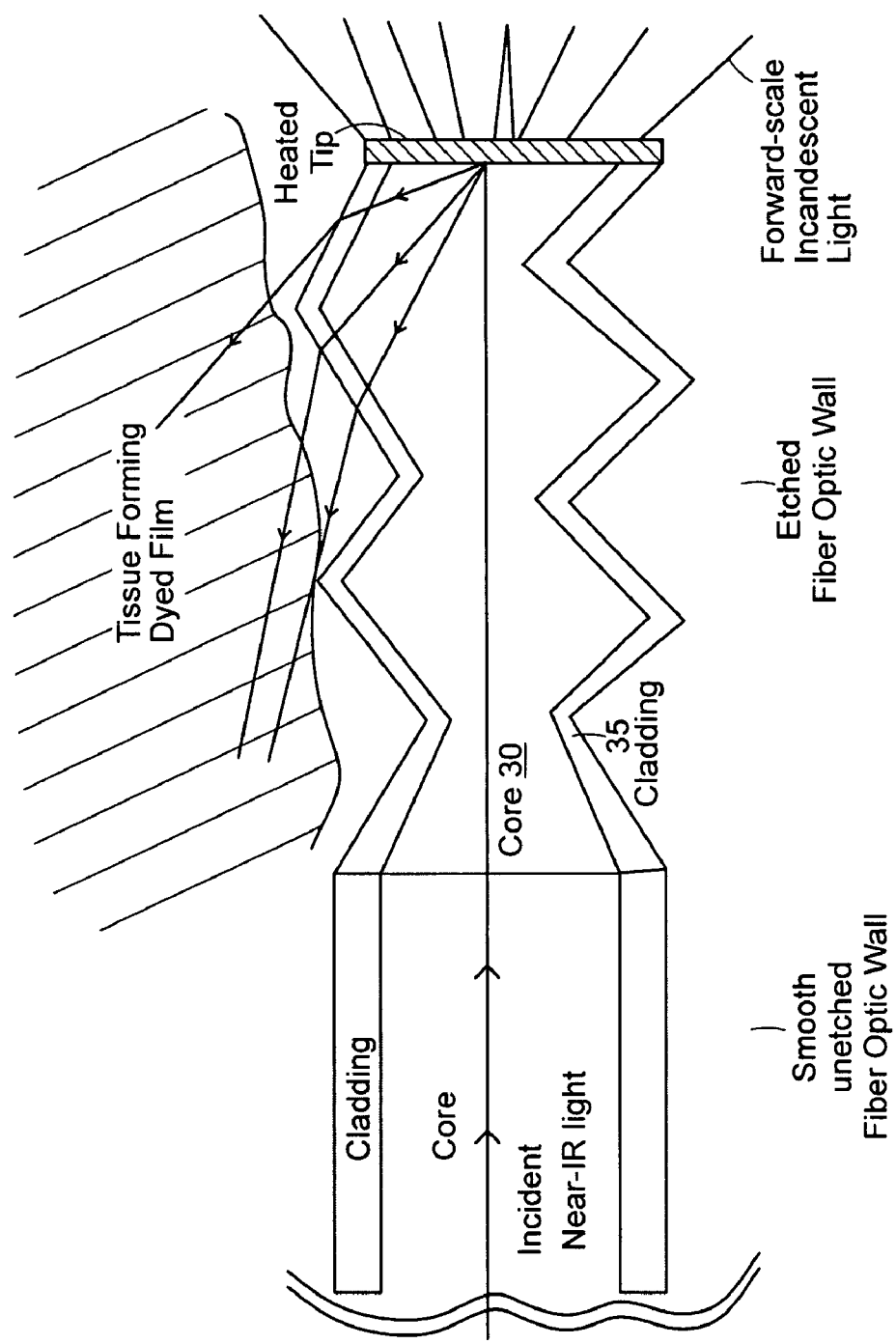
FIG. 7 is a diagram illustrating an especially adapted optical fiber tip according to one of the embodiments of the invention, showing the etched fiber wall and the distal end of the optical fiber.

In the embodiment illustrated in FIG. 7, the effective surface area from which incandescent light is emitted is increased, by modifying the surface geometry of the distal end of the optical fiber in such a way that at least some of the back-propagating incandescent radiation can be diverted and re-directed toward target tissue by transmission through the lateral walls of the optical fiber. Specifically, the surface geometry of the lateral walls of at least a portion of the distal end of the optical fiber is modified, for example by etching, roughening, frosting, or other methods well known in the art, so that at least some of the back-propagating radiation no longer undergoes total internal reflection at the boundary between the core 30 and the cladding 35 of the optical fiber, but rather is transmitted through the lateral walls and towards off-axis target tissue. When such transmitted light has sufficient energy density, then the sidewalls become carbonized, as did the distal tip. Again, at sufficient energy density, the carbonized lateral surfaces generate incandescent radiation, which interacts with the dyed biofilm to effect thermolysis of the biofilm.

FIG. 7 illustrates an exaggerated saw-tooth geometry of a surface of the lateral walls of a portion of the distal end of the optical fiber, modified in the manner described above. FIG. 7 is not drawn to scale, and is meant to provide an exemplary schematic rendition of the etched or otherwise modified surface geometry of the optical fiber lateral walls, which is illustrative of the principles explained above.

As well known, optical fibers are configured so as to guide light from one end of the optical fiber to the other end, by causing the light to undergo total internal reflection at the boundary between the core and the cladding of the optical fiber, so that light is guided through the optical fiber core, from one end of the fiber to the other. The differences between the indices of refraction of the optical fiber core and the optical fiber are such that, for a smooth unmodified surface geometry of the (typically cylindrical) optical fiber, the light traveling through the core is reflected off the cladding glass and stays within the core, so that the fiber core acts as a waveguide for the transmitted light.

As seen in FIG. 7, in one embodiment the smooth surface of the lateral walls of a portion of the distal end is modified or etched in such a way that the surface is no longer smooth, but jagged or serrated. In particular, the etching or serrating of the surface of the optical fiber walls is performed in such a way that the angle of incidence, at which the back-propagating light is incident upon the boundary, is no longer greater than the critical angle, thereby preventing the back-scattering light from undergoing total internal reflection. In this way, back-propagating incandescent light which, in the absence of the modification or etching of the fiber optic wall surface, would have bounced off the cladding and would have stayed within the core to reverse-propagate towards the proximal end of the optical fiber, no longer undergoes total internal reflection at the core-cladding boundary. Rather, the back-propagating radiation incident upon the core-cladding boundary is refracted, so that at least a portion of the back-scattered radiation incident upon the boundary is transmitted through the cladding glass forming the optical fiber wall, and is directed onto the dyed film.

EXAMPLES

The laser used to exemplify the invention was a 830 nm diode laser with a power output of between 800 mW-1200 mW in the Continuous Wave mode of operation, through a 600 micron silica laser delivery fiber. The live human patients (in vivo) all presented with some advanced state of periodontal or periimplant disease and/or active infection. Presented below are data for two representative patients. Notably, the procedure has been performed on 50 patients in the last 24 months. In this time period both the chromophore Methylene Blue and Toludine Blue have been used with successful outcomes, specifically using this invention at the given parameters, in periodontal and periimplant pockets and infections.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein. Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the instant description, numerous specific details are set forth in order to provide a thorough understanding of the present invention. The present invention may be practiced without some or all of these specific details. In other instances, well known process operations have not been described in detail, in order not to unnecessarily obscure the present invention.

Example 1

Treatment of a Recalcitrant 10 mm Periodontal Pocket

Presented as a healthy 24 year old with a recalcitrant 10 mm periodontal pocket on the facial aspect of the maxillary canine (tooth #6) after a regular dental cleaning and scaling. In a minimally invasive procedure, the patient was anesthetized with xylocaine, and the periodontal pocket was infused with 0.1% MB solution via a small bristled brush that easily fits into the volume of the pocket. The MB solution was left for approximately 2 minutes in the area, and then surface irrigation of $H_2O$ was applied.

A 600 nm silica fiber connected to a 830 nm dental diode laser (sold by Lumenis Technologies, Yokneam, Israel) was then activated at 1000 mW and the fiber was placed into the periodontal pocket, where it immediately came in contact with biofilm, tissue, and blood products. The tip of the fiber immediately carbonized, and became incandescent. The fiber (with the secondary quantum emissions emanating from the carbonized tip), was then moved around the three dimensional area of the periodontal pocket for a period of 30 to 45 seconds in rapid movements, never staying in one direct area for more than 1 second at a time. The area was then scaled with traditional gracey periodontal scalers (sold by Hu-Friedy Chicago, Ill.), and then irrigated with copious water. The patient was sent home with administration of 600 mg of Ibuprophen (sold by Wyeth, Madison, N.J.) analgesic given chair-side, and no antibiotics.

Results: At eight days post-op, the periodontal pocket was completely closed, with tissue attachment present that would "blanch" under pressure from a periodontal probe. The area presented with pink and healthy gingival surrounding the previous pocket area. At six weeks, and then four months, the area was only probing at 3 mm (gingival and periodontal health) and the patient was placed on regular six month recall.

Example 2

Treatment of Infected Periimplant Tissue

Presented as a brittle diabetic with an infected titanium implant and a fistula draining the infection. Radiographic appearance detailed 8 mm of lost bone, and generalized radiolucency around the medial half of the implant. Three different antibiotic regimens failed to cure the patient of the infection. The area was surgically opened with a conventional trapezoidal shaped flap, and the infection and biofilm effected area was bathed in a 0.1% MB solution (sold by Vista Dental Products, Racine, Wis.) for approximately 2 minutes. The area was then irrigated with copious $H_2O$, leaving the targeted biofilm behind, and washing away excess stain. A 600 nm silica fiber connected to an 830 nm dental diode laser was then activated at 1200 mW and the fiber was placed in contact with biofilm and blood products and immediately carbonized. The fiber, with the secondary quantum emissions emanating from the carbonized tip were then moved around the near proximity to the area and implant (within ½ mm) for a period of 60 to 90 seconds, never staying in one direct area for more than 2 seconds at a time. The area was then scaled with plastic implant scalers, and irrigated with copious water and sutured closed. The patient was given a 5 day regimen of 500 mg Amoxicillin, (sold by Ranbaxy Pharmaceuticals, Jacksonville, Fla.) three times/day.

Result: At three weeks post-op, the area was completely free of infection with pink and healthy gingival surrounding the area. At four months, a fixed porcelain to gold bridge was cemented onto the implant. At 9 months, the area was still infection free.

What is claimed is:

1. A method for the treatment of periodontal disease in a periodontal or periimplant tissue of a patient having periodontal disease or periimplant disease, the method comprising:

applying a chromophore dye to tissue and biofilm, resulting in stained biofilm and target tissue, wherein the dye preferentially absorbs light energy in an absorption band spectral range;

energizing a laser and sending resulting output laser radiation through an optical fiber comprising a core surrounded by a cladding to an unclad tip of the optical fiber, wherein the laser radiation comprises at least one wavelength in a range from about 800 nm to about 1100 nm;

causing the unclad tip to contact at least a portion of the stained biofilm and target tissue: delivering the laser radiation to the target tissue to form carbonized material; accumulating the carbonized material on the unclad tip;

forming a hot tip from the carbonized material accumulated on the unclad portion of the optical fiber by heating the carbonized material to a temperature of about 600 K to about 1500 K in response to the laser radiation to cause the hot tip to emit secondary quantum emissions of incandescent radiation, at least a portion of said incandescent radiation having wavelengths corresponding to the absorption band spectral range of the dye, and wherein the dye more preferentially absorbs light at wavelengths corresponding the secondary quantum emissions than at wavelengths corresponding to the laser radiation;

irradiating the stained target tissue and biofilm with the secondary quantum emissions emitted from the hot tip; and effecting treatment of the stained biofilm and/or target tissue by the absorption of the secondary quantum emissions by the dye on the stained biofilm and target tissue without causing substantial thermal damage to healthy tissue peripheral to the target area.

2. The method according to claim 1, wherein the laser energy is generated by a diode laser configured and arranged for operating at 500 mW-4000 mW.

3. The method according to claim 1, wherein the dye comprises Methylene Blue or Toludine Blue.

4. The method according to claim 1, wherein the optical fiber contacted with at least a portion of the stained biofilm and target tissue.

5. The method according to claim 4, further including administering a therapeutically effective amount of an antibiotic to the patient having periodontal disease.

6. The method according to claim 1, wherein irradiating the stained biofilm and target tissue is for a therapeutically effective time in a moving pattern to a plurality of locations distributed throughout a treatment volume such that the hot tip does not dwell at any one of the locations for more than about 2 seconds.

7. The method according to claim 1, wherein a solid coagulum of thermolyzed tissue and biofilm is formed when the stained biofilm and target tissue is irradiated with the secondary quantum emissions.

8. The method according to claim 7, further including mechanically removing solid coagulum from a related periodontal pocket or periimplant pocket by periodontal scalers or ultrasonic scalers.

9. The method according to claim 1, wherein effecting treatment of the stained biofilm and/or target tissue by the absorption of the secondary quantum emissions by the dye on the stained biofilm and target tissue without causing substantial thermal damage to healthy tissue peripheral to the target area comprises:

completely coagulating the stained biofilm in response to the secondary quantum emissions; and protecting the healthy tissue peripheral to the target area from thermal damaged caused by the laser radiation by absorbing at least a portion of the laser radiation with the carbonized material accumulated at the hot tip.

10. The method according to claim 9, wherein protecting the healthy tissue peripheral to the target area from thermal damaged caused by the laser radiation by absorbing at least a portion of the laser radiation with the carbonized material accumulated at the hot tip comprises: converting about 70% or more of the power of the laser radiation sent to the unclad tip to local heat at the hot tip.

11. A method according to claim 10, wherein protecting healthy tissue peripheral to the biofilm from substantial thermal damage resulting from the laser radiation comprises: absorbing at least a portion of the laser radiation with the carbonized material accumulated at the hot tip to converting about 70% or more of the power of the laser radiation sent to the unclad tip to local heat at the hot tip.

12. The method of claim 1, wherein the optical fiber extends between a proximal end and a distal end having an unclad portion, wherein:
   the distal end comprises alight emitting end face comprising the unclad tip;
   the core extends along a longitudinal axis to the light emitting end face;
   a portion of the cladding surrounds and forms an interface with the core,
   said portion of the cladding comprises a legion which is at least partially transparent to a portion of the secondary quantum emissions of incandescent radiation transmitted from the end face back through the core the interface of said region with the core is oriented at an angle to the longitudinal axis such that the portion of the secondary incandescent optical energy is incident on the interface at angles less than a critical angle required for total internal reflection secondary quantum emissions of incandescent radiation at the interface.

13. A method for the treatment of bacterial biofilm in a periodontal or periimplant pocket of a patient having periodontal disease or periimplant disease, the method comprising:
   applying a chromophore dye to tissue and biofilm in the pocket, resulting in stained biofilm and target tissue, wherein the dye preferentially absorbs light energy in an absorption band spectral range;
   introducing an end of an optical fiber comprising an unclad tip into the pocket, said optical fiber comprising a core surrounded by cladding and extending to an unclad tip;
   energizing a laser and sending resulting output laser radiation through the optical fiber to the unclad tip, wherein the laser radiation comprises at least one wavelength in a range from about 800 nm to about 1100 nm;
   causing the unclad tip to contact at least a portion of the stained biofilm and target tissue; delivering the laser radiation to the target tissue to form carbonized material; accumulating the carbonized material on the unclad tip;
   forming a hot tip by the carbonized material accumulated on the unclad portion of the optical fiber by heating the carbonized material to a temperature of about 600 K to about 1500 K in response to the laser radiation to cause the hot tip to emit secondary quantum emissions of incandescent radiation, at least a portion of said incandescent radiation having a wavelength corresponding to the absorption band spectral range of the dye, and wherein the dye more preferentially absorbs light at wavelengths corresponding the secondary quantum emissions than at wavelengths corresponding to the laser radiation;
   irradiating the stained target tissue and biofilm with the secondary quantum emissions emitted from the hot tip;
   rapidly moving the hot tip to a plurality of locations distributed throughout the volume of the pocket such that the hot tip does not dwell at any one of the locations for a period of more than about 2 seconds;
   effecting complete coagulation of the entire biofilm within the pocket in response to heat transfer and photobiological events resulting from preferential absorption of the secondary quantum emissions by the dye on the stained biofilm; and
   protecting healthy tissue peripheral to the biofilm from substantial thermal damage resulting from the laser radiation by absorbing at least a portion of the laser radiation with the carbonized material accumulated at the hot tip.

14. The method of claim 13, wherein the optical fiber extends between a proximal end and a distal end having an unclad portion, wherein:
   the distal end comprises alight emitting end face comprising the unclad tip;
   the core extends along a longitudinal axis to the light emitting end face;
   a portion of the cladding surrounds and forms an interface with the core,
   said portion of the cladding comprises a region which is at least partially transparent to a portion of the secondary quantum emissions of incandescent radiation transmitted from the end face back through the core, the interface of said region with the core is oriented at an angle to the longitudinal axis such that the portion of the secondary incandescent optical energy is incident on the interface at angles less than a critical angle required for total internal reflection secondary quantum emissions of incandescent radiation at the interface.

* * * * *